(12) United States Patent
Morath et al.

(10) Patent No.: US 7,050,178 B2
(45) Date of Patent: May 23, 2006

(54) METHOD AND APPARATUS FOR INCREASING SIGNAL TO NOISE RATIO IN A PHOTOACOUSTIC FILM THICKNESS MEASUREMENT SYSTEM

(75) Inventors: Christopher Morath, Morristown, NJ (US); Robert J. Stoner, Duxbury, MA (US)

(73) Assignee: Rudolph Technologies, Inc., Flanders, NJ (US)

( * ) Notice: Subject to any disclaimer, the term of this patent is extended or adjusted under 35 U.S.C. 154(b) by 340 days.

(21) Appl. No.: 10/194,169

(22) Filed: Jul. 12, 2002

(65) Prior Publication Data

US 2003/0020929 A1      Jan. 30, 2003

Related U.S. Application Data

(60) Provisional application No. 60/305,175, filed on Jul. 13, 2001.

(51) Int. Cl.
*G01B 11/28* (2006.01)
*G01J 4/00* (2006.01)

(52) U.S. Cl. ..................... 356/630; 356/364
(58) Field of Classification Search ........ 356/630–632, 356/364, 365, 369, 370; 250/225; 73/760, 73/800, 801
See application file for complete search history.

(56) References Cited

U.S. PATENT DOCUMENTS

| | | | |
|---|---|---|---|
| 4,710,030 A | 12/1987 | Tauc et al. | 356/432 |
| 5,379,109 A | 1/1995 | Gaskill et al. | 356/445 |
| 5,546,811 A | 8/1996 | Roagers et al. | 73/800 |
| 5,693,938 A | 12/1997 | Marchman et al. | 250/234 |
| 5,748,317 A * | 5/1998 | Maris et al. | 356/502 |
| 5,844,684 A | 12/1998 | Maris et al. | 356/432 |
| 5,864,393 A | 1/1999 | Maris | 356/28 |
| 5,959,735 A | 9/1999 | Maris et al. | 356/381 |
| 6,008,906 A | 12/1999 | Maris | 356/432 |
| 6,028,870 A * | 2/2000 | Deutsch et al. | 372/25 |
| 6,038,026 A | 3/2000 | Maris | 356/357 |
| 6,108,087 A | 8/2000 | Nikoonahad et al. | 356/359 |
| 6,643,005 B1 * | 11/2003 | Hale et al. | 356/237.1 |
| 6,754,249 B1 * | 6/2004 | Schmid et al. | 372/106 |

OTHER PUBLICATIONS

Nen-Wen Pu et al, "Picosecond Ultrasonic Study of Mo/Si Multilayer Structures Using An Alternating-Pump Technique", Applied Physics Letters, vol. 74, No. 2, Jan. 11, 1999, pp. 320-322.

* cited by examiner

*Primary Examiner*—Gregory J. Toatley, Jr.
*Assistant Examiner*—Gordon J. Stock, Jr.
(74) *Attorney, Agent, or Firm*—Harrington & Smith, LLP

(57) ABSTRACT

An apparatus for improving the signal to noise ratio of measurements of the thickness of layers in a thin film stack uses a photoacoustic measurement system that includes a time differentiation system for inducing a delay in pump beam pulses. The time differentiation system uses, among other things, a birefringent element and other elements to control the polarization of pump beam pulses. Use of the apparatus involves applying a time varying voltage to an electro-optic modulator driver and setting a time differentiation step; or, in another embodiment, applying a time varying voltage to an electro-optic modulator to induce a fixed time delay delta-t between a vertically polarized pulse and a horizontally polarized pulse. The high frequency operation of the system provides for improved determinations of film thickness.

18 Claims, 6 Drawing Sheets

METHOD AND APPARATUS FOR INCREASING SIGNAL TO NOISE RATIO IN A PHOTOACOUSTIC FILM THICKNESS MEASUREMENT SYSTEM

CLAIM OF PRIORITY FROM COPENDING APPLICATION

Priority is herewith claimed under 35 U.S.C. §119(e) from co-pending U.S. Provisional Patent Application 60/305,175, filed Jul. 13, 2001, entitled "Method And Apparatus For Increasing Signal To Noise Ratio In A Photoacoustic Film Thickness Measurement System," by Chris Morath. The disclosure of U.S. Provisional Patent Application 60/305, 175 is incorporated by reference in its entirety.

TECHNICAL FIELD

These teachings relate generally to optical metrology methods, apparatus and, more specifically, to metrology systems for characterizing integrated circuits and various types of films disposed on integrated circuits.

BACKGROUND

The increasing sophistication of semiconductor technology has resulted in a significant shift away from aluminum as the dominant metal in multi-level metallization processes. Copper has been proven in limited production volumes, and is likely to become the metal of choice in future designs. The differences between aluminum and copper present unique challenges and opportunities for manufacturers of metrology systems. In parallel with the development of copper-based metallization processes is the ongoing reduction in minimum line widths. Both singularly and together these two factors present a number of challenges and problems in the field of non-destructive optical metrology.

Presently, there are several methods for depositing thin films of copper for back end of the line (BEOL) metallization processes. The dominant method currently involves depositing a seed layer of copper on top of a barrier metal such as tantalum, then electroplating a thick layer of copper on top of the seed layer. Once deposited, it is important to be able to verify that the deposited metal is within specifications. Therefore, what is needed is a technique to accurately measure the thickness of metal films.

The traditional method for measuring the thickness of copper films is the four-point probe method. With this technique, originally developed in the 1950s, an array of four pointed probes arranged in a straight line is pressed into the conductive copper film. Current is applied to one outer probe, and returned via the opposite outer probe. A measurement of the voltage between the middle two probes is combined with the amount of current and knowledge of the bulk resistivity of the film to determine the thickness of the film. However, this method requires that the probes penetrate the surface of the conductive layer. Doing so causes scratches, and can also cause small amounts of particulates to form that can cause defects elsewhere on the wafer. Additionally, this method requires a priori knowledge of the bulk resistivity of the film. The bulk resistivity depends in part on the grain structure and orientation of the grains in the metal, and a problem that has challenged process engineers working on copper metallization processes is that the grain structure and orientation of the grains in copper changes as a function of time, even if the metallized wafers are left at room temperature. Therefore, what is also needed is a non-contact technique to measure metal films.

A measurement using an existing metrology system produces a signal that results from inducing changes in reflectivity caused by stress fields propagating into the sample. As the stress field encounters acoustic impedance mismatches, a portion of the stress field scatters back toward the surface. A probe beam monitoring the time dependent change in reflectivity detects changes in the reflectivity as the stress fields propagate. However, this signal is small, and the presence of noise complicates analysis methods. A particularly problematic type of noise is low-frequency (within the data acquisition bandwidth) "multiplicative noise" that arises from power fluctuations of the laser, vibration of the sample or system optics and temperature fluctuations or air currents in the system that steer the beams. These 1/f noise sources can be reduced by proper laser selection, vibration isolation of the measurement system, and shielding the air currents around the system. However, the resulting level of noise may still be too large to make repeatable measurements on certain metal samples with extremely thin layers or thin buried layers. Thus, what is also needed is an improved technique to accurately extract film thicknesses from measured data when there is noise in the data. A technique to suppress 1/f noise present in the measurement data is needed as well.

Furthermore, existing methods for extracting layer thickness information from the measurement data are adequate for many cases. However, if there is a particularly thin layer adjacent to a thick layer, the high-frequency acoustic signal reflecting from the thin layer may be severely attenuated and easily obscured by noise. What is thus also needed is a technique to resolve fine structure in the measurement data.

Metrology systems have been devised that are intended to improve upon limitations described in the foregoing. In many cases, the acoustic features of interest ride on a large amplitude slowly-varying thermal response or "background signal." Time-differentiating the total signal numerically can remove the background but does not improve the acoustic signal to noise content. On the other hand, if the time-differentiation is done optically at a frequency above the 1/f noise region (several kHz for the air currents and vibration, up to about 1 MHz for the laser noise), the background signal is "stripped" without contributing to the multiplicative noise. Thus an optical time-differentiator can decrease noise in the data, leading to improved measurement repeatability for a given data averaging time.

Methods for measuring the derivative with respect to time of the response of a sample as a continuous function of time are known. In these methods, path length may be adjusted by means of the mechanical delay line, and in addition path length may be rapidly modulated at a frequency $f_{path}$ by a small amount. One method described for modulating was to mount a mirror in one of the beam paths on a piezoelectric transducer, the mirror oscillating along an axis parallel to the direction of propagation of the beam. In this method, the frequency $f_{DIFF}$, and the maximum modulated time delay is limited by the characteristics of the piezoelectric actuator. A typical maximum $f_{DIFF}$ is a few kHz, and a typical modulated delay is 100 fsec. By folding the beam path to effect multiple reflections from the oscillating mirror and mounting the mirror on a cantilever, the modulated delay may be increased to several picoseconds. In practice, however, this may cause the beam to "wander" significantly in response to the modulation, and furthermore may generate significant vibrations in the measurement apparatus, thus degrading the repeatability and accuracy of a measurement. Another scheme employs a rapidly spinning transparent block. Yet another scheme employs a rapidly spinning wheel with transparent sections which provide two or more optical path lengths. All of these schemes suffer from drawbacks similar to those described for the piezoelectric actuator, and in addition may significantly modulate the position, direction, quality, intensity and polarization of the laser beam.

Exemplary United States patents that are relevant to the system(s) of interest herein are now introduced.

U.S. Pat. No. 6,008,906, "Optical method for the characterization of the electrical properties of semiconductors and insulating films," describes a method for characterizing a sample that includes the steps of (a) providing a semiconductor material; (b) applying at least one of an electric field, a pulsed or cw light source, a change in temperature and/or a change in pump pulse intensity to the semiconductor material; (c) absorbing pump light pulses in a portion of the semiconductor material and measuring changes in optical constants as indicated by probe light pulses applied at some time t following the absorption of the pump light pulses; and (e) associating a measured change in the optical constants with at least one of a surface charge, dopant concentration, trap density, or minority carrier lifetime.

U.S. Pat. No. 4,710,030, "Optical generator and detector of stress pulses," describes an optical stress pulse generation and detection system for non-destructively measuring physical properties of a sample. This system uses a pump beam having short duration radiation pulses having an intensity and at least one wavelength selected to non-destructively generate a stress pulse in a sample. The system directs the non-destructive pump beam to a surface of the sample to generate the stress pulse. The optical stress pulse generation and detection system also uses a probe radiation beam and guides the probe beam to a location at the sample to intercept the stress pulse. The change in optical constants induced by the stress pulse is detected by observing the probe beam after it intercepts the stress pulse.

U.S. Pat. No. 5,379,109, "Method and apparatus for non-destructively measuring local resistivity of semiconductors," describes an apparatus for non-destructively measuring the resistivity of a semiconductor, such as InP. The system has light sources for illuminating a pre-selected portion of the semiconductor with first and second light beams, each of a pre-selected single wavelength. The first light beam operates to excite the semiconductor by photo-injecting carriers, and the second light beam bombards the local portion of the semiconductor with a pre-selected photon energy. The system measures a fractional change in reflectance of the second light beam responsive to the first light beam, and records this fractional change in reflectance for various values of photon energy of the second light beam, to generate a photoreflectance line-shape. The photoreflectance line-shape is used to calculate a photoreflectance line-shape phase angle, which is used to determine the resistivity of the pre-selected portion of the semiconductor.

U.S. Pat. No. 5,546,811, "Optical measurements of stress in thin film materials", describes a method for determining the residual stress in an unsupported region of a thin film. The method includes the steps of (a) optically exciting the film with a spatially and temporally varying optical excitation field to launch counter-propagating acoustic modes along at least one wave vector; (b) diffracting a portion of an optical probe field off the excited acoustic modes to generate a time-dependent signal field at the excitation wave vector; (c) detecting the signal field to generate a time-dependent, light-induced signal; (d) analyzing the light-induced signal to determine the frequencies of the acoustic modes; (e) partially determining the dispersion of at least one mode; and, (f) comparing the measured dispersion to that calculated using a mathematical model to allow the residual stress properties of the unsupported region of the film to be determined.

U.S. Pat. No. 5,693,938 "Optical probe microscope having a fiber optic tip that receives both a dither motion and a scanning motion, for nondestructive metrology of large sample surfaces", describes an optical probe microscope that includes an optical fiber oriented in a vertical direction. The fiber has a tip that emits light onto a horizontal surface of a sample to be measured. This surface can have both desired and undesired departures from planarity. An electromechanical device for imparting dither motion to the fiber tip is superposed on another electromechanical device for imparting two-dimensional horizontal scanning motion to the fiber tip. The dither motion has a much higher frequency than that of the scanning motion. Between successive scans, another device moves the sample itself from one horizontal position to another. A microscope receives the optical radiation either transmitted or reflected by the sample surface. The microscope forms a (magnified) image of this received optical radiation on the surface of an optical image position detector. The surface of this detector has a relatively large area compared with that of the (magnified) image. The resulting electrical signal developed by the detector provides desired information concerning the scanning position of the fiber tip. Also, this electrical signal is processed and fed back to a vertical pusher that maintains constant the distance of the fiber tip from the sample surface.

U.S. Pat. No. 6,038,026, "Apparatus and method for the determination of grain size in thin films," describes a method for the determination of grain size in a thin film sample having steps of measuring first and second changes in the optical response of the thin film, comparing the first and second changes to find the attenuation of a propagating disturbance in the film and associating the attenuation of the disturbance to the grain size of the film. The second change in optical response is time delayed from the first change in optical response.

U.S. Pat. No. 5,959,735, "Optical stress generator and detector," describes a system for the characterization of thin films, as well as interfaces between thin films, through measurements of their mechanical and thermal properties. In the system light is absorbed in a thin film or in a structure made up of several thin films, and the change in optical transmission or reflection is measured and analyzed. The change in reflection or transmission is used to give information about the ultrasonic waves that are produced in the structure. The information that is obtained can include (a) determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects.

U.S. Pat. No. 5,844,684, "Optical method for determining the mechanical properties of a material," describes a system and method for characterizing a sample. The method includes steps of (a) acquiring data from the sample using at least one probe beam wavelength to measure, for times less than a few nanoseconds, a change in the reflectivity of the sample induced by a pump beam; (b) analyzing the data to determine at least one material property by comparing a background signal component of the data with data obtained for a similar delay time range from one or more samples prepared under conditions known to give rise to certain physical and chemical material properties; and (c) analyzing a component of the measured time dependent reflectivity caused by ultrasonic waves generated by the pump beam using the at least one determined material property. The first step of analyzing may include a step of interpolating between reference samples to obtain an intermediate set of material properties. The material properties may include sound velocity, density, and optical constants. In one embodiment, only a correlation is made with the background signal, and at least one of the structural phase, grain orientation, and stoichiometry is determined.

A further example of a photoacoustic system is provided in the article "Picosecond Ultrasonic Study Of Mo/Si Multilayer Structures Using An Alternating-Pump Technique." Nen-Wen Pu et al. in Applied Physics Letters, Volume 74, Number 2, 11 Jan. 1999, pgs 320–322.

The system disclosed in this article makes use of a pump-and-probe transient reflectivity technique in which the acoustic waves are impulsively excited by optical absorption of an ultrashort "pump" laser pulse and detected as a reflectivity change of the time-delayed "probe" laser beam. The article discloses use of an acousto-optic modulator (AOM) and other components to provide for enhanced signal to noise ratios, and improved sensitivity. However, as this system relies upon acousto-optic diffraction of the pump beam, the ability to take measurements at different wavelengths is limited. More specifically, limitations of this system include the need to vary the pump beam diffraction angle with wavelength, and the limited useful wavelength range of commonly available acousto-optic materials (e.g. $TeO_2$, $SiO_2$). Therefore, the versatility of this system is also limited.

As improving semiconductor technology has driven toward ever thinner layers of varied materials, frequently appearing in the presence of thick layers, a challenge is presented to existing metrology systems. What are needed are improved metrology systems for measurement of thin layers of films, such as the one presented herein.

SUMMARY OF THE PREFERRED EMBODIMENTS

The foregoing and other problems are overcome, and other advantages are realized, in accordance with the presently preferred embodiments of these teachings.

The apparatus and methods disclosed herein make use of and provide advancements to photoacoustic metrology systems. Such systems, as presently exist and as are related to this invention use, among other things, a radiation source (such as a laser) to produce a pump beam and a probe beam used to induce and detect optical stress in a sample.

The present invention extends the maximum frequency $f_{DIFF}$ up to hundreds of MHz, or higher. The teachings herein therefore allow for time delays of up to hundreds of picoseconds and substantially eliminate spurious modulation of the position, direction, spectral content, quality, intensity and polarization of the laser beam.

The system includes a polarization rotation device for rotating the polarization of a linearly polarized radiation beam emitted by a laser through ninety degrees, and further includes a delay device for delaying one beam polarization with respect to another beam polarization, thereby creating delayed pulses in the beam.

The invention includes an apparatus and method for examining locations on a sample (herein referred to interchangeably as a "wafer" or a "sample") and making a measurement of the thickness of layers of thin films in the sample. The apparatus includes a photoacoustic measurement system equipped with components for causing time differentiation of the pump beam. The method involves dithering of the laser beam used in the measurement process over time.

One difference between the present invention and the prior art is an apparatus for improving the signal to noise ratio of measurements of the thickness of layers in a thin film stack using a photoacoustic measurement system that includes a birefringent crystal driven by an electro-optic modulator to sweep the measurement in time about a quiescent time determined by the instantaneous position of a moveable retroreflector.

An aspect of the invention is the use of a high-frequency optical time-differentiation system to remove the background signal (e.g. thermal) and low-frequency acoustic components from the photo-acoustic signal, thereby decreasing noise in the acoustic measurement and increasing the thickness measurement sensitivity.

Another aspect of the invention is the use of an optical time-differentiation system and an optimized derivative time step to enhance acoustic features on the basis of frequency, improving selectivity for thin layers (reflecting high frequency acoustic components) buried underneath thicker layers.

Another aspect of the invention is an apparatus for improving the signal to noise ratio of measurements of the thickness of layers in a thin film stack using a photoacoustic measurement system that includes an electo-optic differentiator to sweep the measurement in time about a quiescent time determined by the instantaneous position of a moveable retroreflector.

Another aspect of the invention is an apparatus for improving the signal to noise ratio of measurements of the thickness of layers in a thin film stack using a photoacoustic measurement system that includes an electo-optic modulator and birefringent crystal.

The method disclosed herein includes loading a sample from a cassette to a measurement stage; bringing an optical assembly of the measurement system into focus; aligning the beam spot with a measurement site on the sample; in one embodiment applying a time-varying voltage to an eletro-optic modulator (EOM) according to a predetermined recipe and setting a time differentiation step, and in another embodiment applying a time-varying voltage to an EOM signal generator according to a predetermined recipe to cause a birefringent crystal to induce a lag between a first and a second pulse of polarized light; making a measurement; recording the measurement data; analyzing the measurement data to determine an average film thickness in the measurement area; and unloading the sample back to the cassette.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein.

DETAILED DESCRIPTION OF THE PREFERRED EMBODIMENTS

These teachings provide an apparatus for, and a method of, improving thickness measurements of a film, or multiple layers of film forming a layered film (herein also a "stacked film") without contacting the film. An example of films that may be measured by the apparatus and methods disclosed herein includes films that form wafers or semiconductor components. Those skilled in the art will recognize that deviations from the teachings disclosed herein may be realized, while remaining within the scope of this invention.

The apparatus includes a modulator that provides for modulating the optical path length in one arm of an optical metrology system up to relatively high frequencies, such as those ranging between a few kHz (about one kHz), up to hundreds of MHz. The use of the method disclosed herein provides for precise calculation of film thickness.

Optical Metrology System

Figure 1:
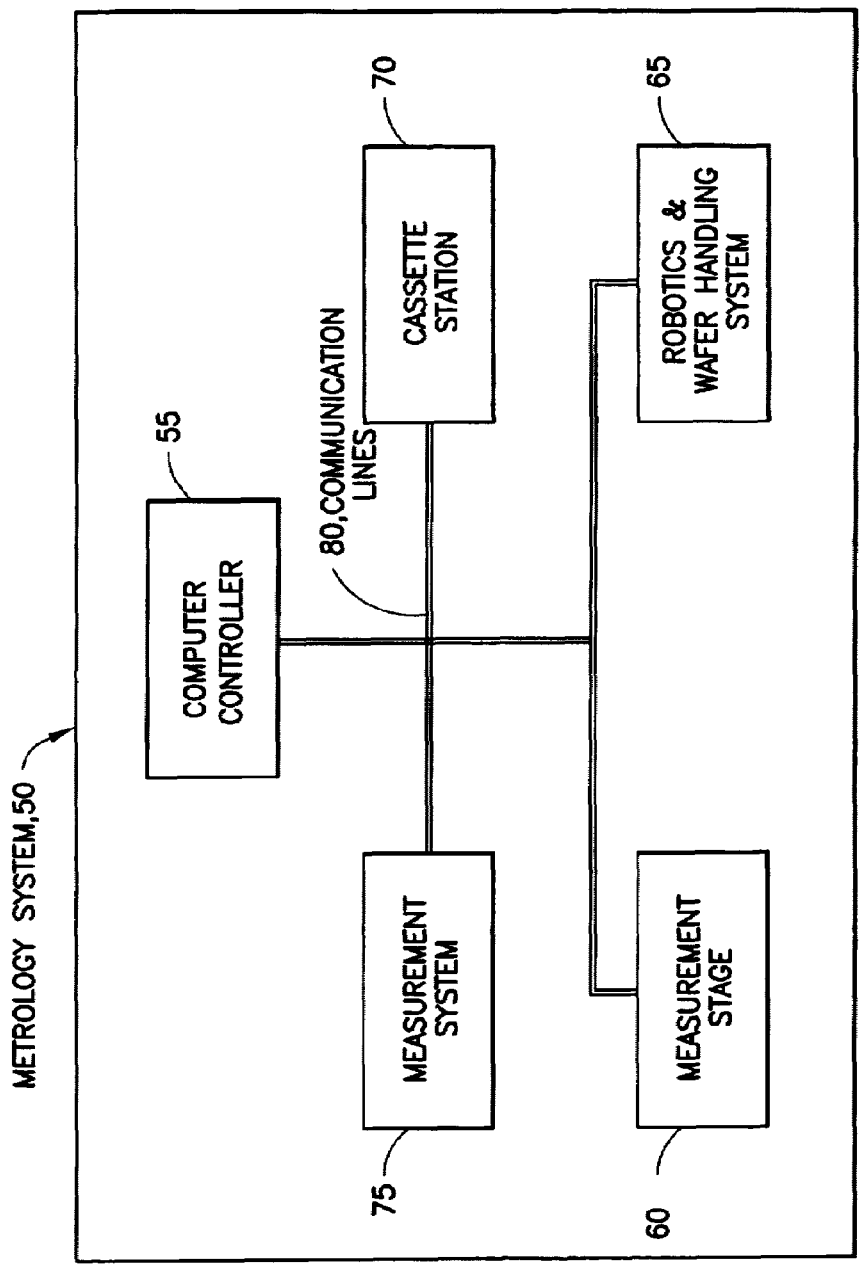
FIG. 1 is a block diagram showing the major components of a metrology system that includes a measurement stage.

FIG. 1 shows a metrology system 50 that includes a controller 55, communication lines 80, a cassette station 70, a robotics and wafer handling system 65, a measurement stage 60, and a measurement system 75.

Controller 55 is electrically connected to measurement system 75, measurement stage 60, robotics and wafer handling system 65, and cassette station 70 with communication lines 80.

The controller 55 includes a computing device, such as a personal computer, with a processor and a memory and other features (not shown).

In operation, controller 55 sends an instruction to the robotics and wafer handling system 65 to extract a wafer from cassette station 70, and to position the wafer on the measurement stage 60. The controller 55 then issues commands to the measurement stage 60 to position the wafer relative to the measurement system 75 so that measurements can be made at a predetermined location. The controller 55 then issues commands to the measurement system 75 to make a measurement and display the results of the measurement. Once the measurement is complete, controller 55 issues instructions to the robotics and wafer handling system 65 to return the wafer to the cassette station 70.

The measurement stage 60 includes a test surface upon which the wafer is placed for measurements, and translation stages to provide wafer manipulation in three degrees of freedom. The preferred embodiment includes two linear stages arranged at right angles with respect to on another and in the plane of the test surface, and another linear stage to move the wafer in the direction of the measurement system.

Figure 2:
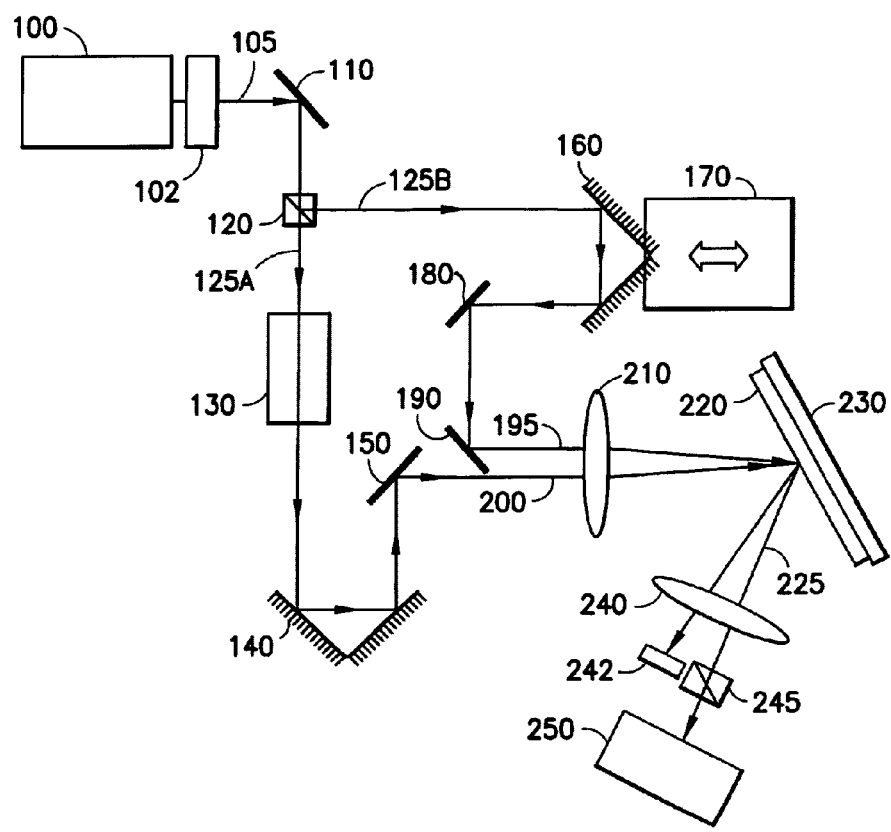
FIG. 2 is a schematic diagram of a first embodiment of a photoacoustic film thickness measurement system depicting the optical pathways.

FIG. 2 is a schematic diagram of a photoacoustic film thickness system 75 that includes, as arranged in FIG. 2, a pulsed light source 100, a sample stage 220, a stage/vacuum chuck 230, a first probe steering mirror 180, a pump beam steering mirror 150, a first steering mirror 110, a pump-probe beamsplitter 120, and pump beam time differentiation assembly 130. Additionally, photoacoustic system 75 includes a probe retroreflector 160, a delay scanning stage 170, a beam dump 242, and a detector 250. Furthermore, photoacoustic measurement system 75 includes a linear pump-discriminating polarizer 245, a harmonic generator wavelength selector (wavelength selector) 102, a projecting lens 210, a collimating lens 240, a pump retroreflector 140, and a second probe steering mirror 190.

Pulsed light source 100 is preferably a titanium-sapphire laser operating at 80 MHz and emitting light at 800 nm. In one embodiment, the laser can be alternatively configured with a frequency doubling birefringent crystal to emit laser beam 105 at 400 nm. Thus, system operation at two different wavelengths is possible.

In operation, pulsed light source 100 emits laser beam 105 where it is re-directed by first steering mirror 110. The pump beam and probe beam beamsplitter 120 splits incident laser beam pulse (preferably of picosecond or shorter duration) into pump beam 125A and probe beam 125B. In one embodiment, the time differentiation system 130 converts pump pulse train 125A into pump pulse train 200 consisting of two series of pump pulses that are prepared with identical spatial and polarization attributes, but are time shifted with respect to each other by an amount delta-t, and whose relative amplitudes are time-modulated at a frequency $f_{DIFF}$ of about one kHz to about ten MHz, or alternatively from about 1 kHz to about 1 GHz.

Pump beam retroreflector 140 and pump beam steering mirror 150 direct time-modulated pump beam 200 towards projecting lens 210.

Probe beam 125B is transmitted to probe retroreflector 160 where delay scanning stage 170 is used to modify the length of the beam path of probe beam 125B relative to the length of modulated pump beam 200, thus forming time delayed probe beam 195.

Delayed probe beam 195 and modulated pump beam 200 propagate through projecting lens 210 and finally onto sample 220. The stage/vacuum chuck 230 acts as a positioning unit for the sample wafer and is preferably a multiple-degree of freedom stage that is adjustable in height (z-axis), position (x and y-axes), and tilt (q), and allows motor controlled positioning of a portion of the sample relative to the modulated pump beam 200 and delayed probe beam 195. The z-axis is used to translate the sample vertically into the focus region of the pump and probe beams, the x and y-axes translate the sample parallel to the focal plane, and the tilt axes adjust the orientation of the sample 220 to establish a desired angle of incidence for the probe beam.

Modulated pump beam 200 and delayed probe beam 195 propagate through collimating lens 240 where modulated pump beam 200 is gathered by beam dump 242. Pump-discriminating polarizer 245 isolates reflected probe beam 225 from modulated pump beam 200. Detector 250 converts reflected probe beam 225 into a signal versus delay stage 170 position. This signal is demodulated and sent to controller 55 for analysis (e.g. to determine film thickness). One embodiment of the time differentiation assembly 130 is shown in more detail in FIG. 3.

Figure 3:
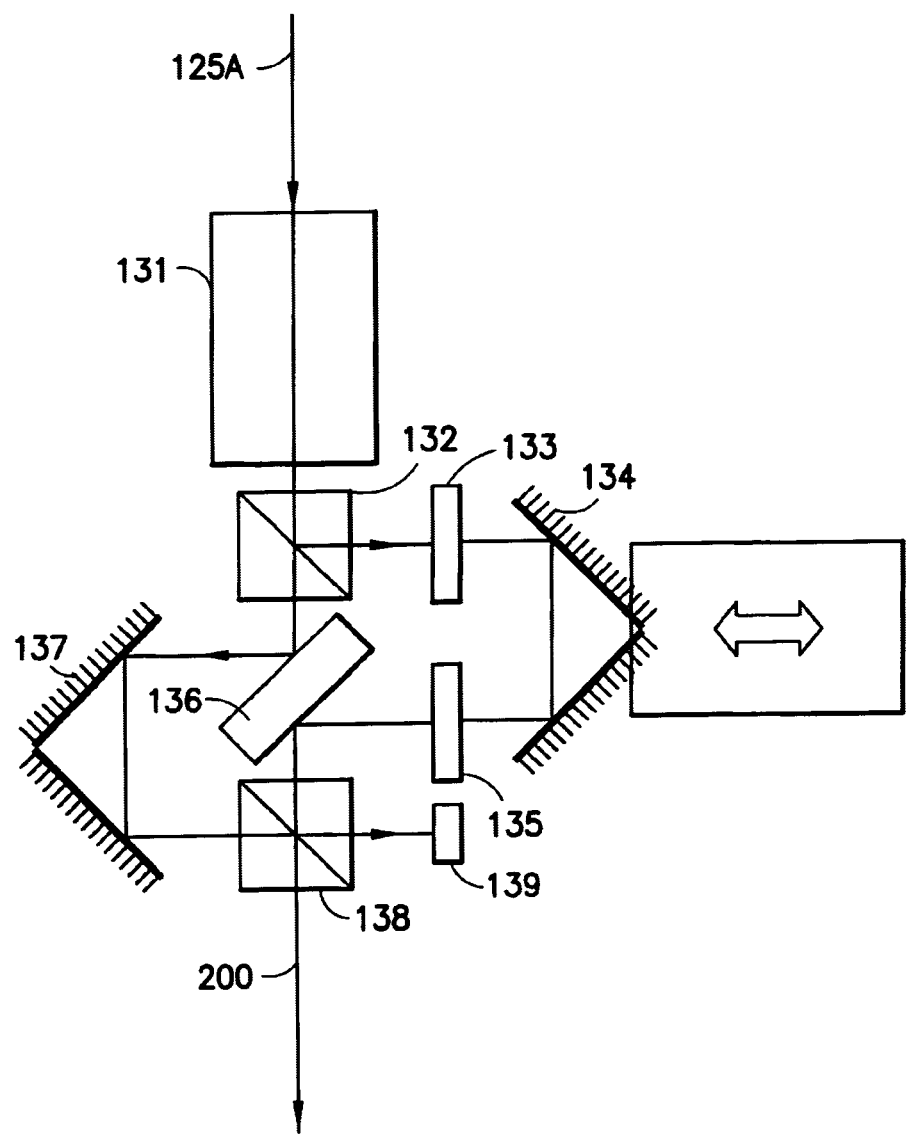
FIG. 3 is a schematic diagram of an time differentiation assembly included within the photoacoustic film thickness measurement system shown in FIG. 2.

FIG. 3 shows the preferred embodiment of the time-differentiation system 130. In this embodiment, the time-differentiation system 130 includes an electro-optic modulator (EOM) 131; a polarizing beam splitting cube 132 that reflects vertically polarized light, transmits horizontally polarized light, and a beam shutter 133 which is set in the OPEN position for time differentiation mode. The EOM, when electrically driven through a "half-wave" voltage cycle (typically from about zero to several hundred volts), will rotate the polarization of the exiting pump beam between horizontal and vertical orientations at a frequency in the range of about one kHz up to hundreds of MHz. When in the CLOSED position, beam shutter 133 blocks one pump beam path, making the optics configuration identical to an electro-optic modulator followed by a polarizer, thereby yielding an amplitude-modulated pump beam 200 as per the technique described in U.S. Pat. No. 5,748,318 "Optical Stress Generator and Detector" by Maris et al., and issued on May. 5, 1998, herein incorporated by reference. Thus, this preferred embodiment allows for rapid and automatic switching between the time-differentiation mode and the mode presented by Maris et al.

Other components shown in FIG. 3 include a retroreflector 134 on an adjustable translation stage. The stage position is set to obtain a specified time delay difference delta-t between the two pump beam paths in the approximate range of 0.1 psec to 10 psec (although up to hundreds of psec are possible). Time delay difference delta-t can be adjusted according to the signal feature of interest for the sample under study. A half-wave plate 135 is included. The angle of the half-wave plate 135 is set to rotate the beam's polarization to horizontal for recombination with the beam traveling the other path at the recombining beamsplitter 138. A steering mirror 136 is included with a fixed retroreflector 137, and the recombining beamsplitter 138. The recombining beamsplitter 138 reflects 50% of beam coming from retroreflector 137, and transmits 50% of beam coming from mirror 135. A beam dump 139 is also included.

Other embodiments or versions of the time differentiation system 130 used to delay the pump beam are now discussed.

A second embodiment of time differentiator 130 is described in FIGS. 4–8. A first version of the second embodiment is pictured in FIG. 4. The pump beam passes through a system consisting of half waveplate (HWP1), a birefringent element (BRE), and a second half waveplate (HWP2). HWP1 and HWP2 are controlled such that they are always in a common state which may be ON or OFF. In the ON state, each HWP causes a rotation by plus or minus ninety degrees of the beam polarization. In the ON state, therefore, the optical axis of each HWP makes an angle of forty-five degrees with the direction of polarization of the pump beam. The HWPs have no effect on the beam polarization when in the OFF state. The BRE is aligned such that light of either polarization will enter and emerge from it in substantially the same location, that is, the beams propagate along a substantially common axis. The BRE exhibits a polarization dependent refractive index n; the values corresponding to the two orthogonal beam polarizations are herein denoted as n1 and n2. It is preferred that the BRE and HWPs have optical coatings in order to minimize the dependence of the intensity of the transmitted beam on polarization. The optical path length through the BRE depends on, among other things, the polarization of the beam. Accordingly, the transit time difference delta-t for the two polarizations is delta-t=d(n1−n2)/c, where d is the physical thickness of the BRE along the direction of propagation of the radiation beam, c is the speed of light in vacuum, and n1 and n2 are the indices of refraction in the BRE for the two polarizations (assuming n1 is greater than n2). In the case where n1 and n2 are the polarizations of the beam entering the BRE, when HWP1 and HWP2 are in the ON and OFF states respectively, the ON state beam will be delayed relative to the OFF state beam. Because the net effect of HWP1 and HWP2 is a zero degree or 180 degree rotation of the beam polarization, the incident and emergent beams are polarized parallel to a common linear axis. A system providing a delay of about one picosecond preferably uses a BRE made from commonly available materials (for example, calcite or potassium dideuterium phosphate, known as "KDP") having a thickness of approximately one millimeter. The BRE thickness may be selected to provide a desired delay. To achieve very long delays, a suitable number of BREs may be placed in series.

Figure 4A:
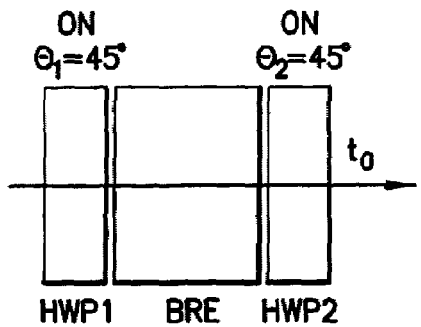
FIGS. 4a–b, collectively referred to as FIG. 4, are schematic diagrams of a birefringent element with first and second half wave plates.
Figure 4B:
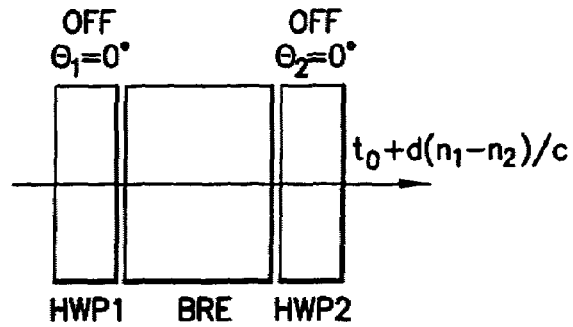
Figure 5A:
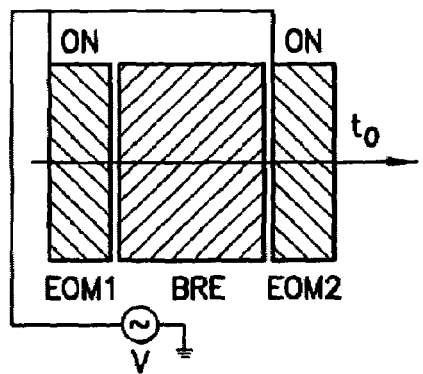
FIGS. 5a–b, collectively referred to as FIG. 5, are schematic diagrams that depict use of a birefringent element in an electrically controlled embodiment.
Figure 5B:
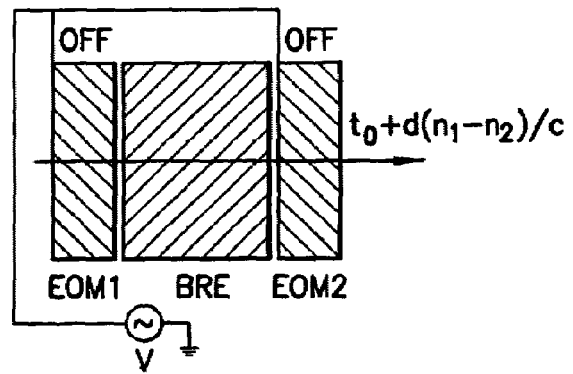

The version of the second embodiment described above is depicted in FIG. 4. In FIG. 4a the propagation time for the radiation beam through the system is t0; whereas in FIG. 4b the propagation time is t0+d(n1−n2)/c. Hence the time difference is given by delta-t=+d(n1−n2)/c Another version of the second embodiment, shown in FIG. 5, features an electro-optic modulator (EOM1) intended to function as a half waveplate (HWP) for linearly polarized light. The EOM1 is configured for a wavelength that is at or close to the center of the distribution of wavelengths in the beam to be delayed. The EOM may be toggled by application of a suitable electrical control signal used to cause switching between an ON state, in which the EOM functions as a HWP and therefore rotating the beam polarization by ninety degrees, and an OFF state in which the EOM preserves the polarization of the input beam. After passing through EOM1 the beam passes through a birefringent element (BRE). The BRE is so oriented that light in either polarization state follows a substantially common path. After the BRE the beam is directed through a second electro-optic modulator EOM2, which is configured to be in the same state (ON or OFF) as EOM1. In one version, the electrical control signals applied to the EOMs have identical phase and frequency. As a result, the beam exiting EOM2 has the same polarization as the beam entering EOM1. The propagation time for the beam through the system will assume two different values depending on the states of EOM1 and EOM2. Electro-optic modulators that allow square wave switching at frequencies up to hundreds of MHz are suited for use in this invention, and are readily available. Other higher frequency EOMs may be used to practice the teachings herein, such as EOMs that operate at a frequency of about 1 GHz. Use of the higher frequency EOM, whether "off the shelf" or specially developed for use with the teachings herein, therefore provides for operation at higher frequencies than previously attainable.

Figures 6, 7:
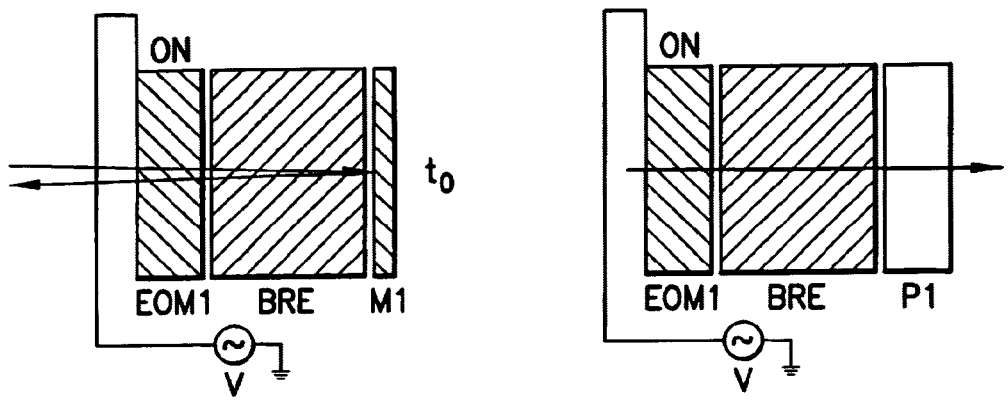
FIG. 6 is a schematic diagram of a single polarization rotator embodiment.
FIG. 7 is a schematic diagram of a non-reflective embodiment with a single polarization rotator with an output polarizer.

A preferred version of the second embodiment employs only a single HWP and a mirror M1 that is used to reflect the beam back through the BRE and HWP as shown in FIG. 6. Examples of devices suited for use as a single HWP include, but are not limited to, a fixed linear retarder, and an EOM. In this embodiment, HWP functions as HWP1 and HWP2, as discussed in relation to FIG. 4. The embodiment shown in FIG. 6 does not require one to drive HWP1 and HWP2 in synchronism. In this embodiment, the delay is now calculated as 2d(n1−n2)/c, since this beam passes through the BRE twice. Alternatively, it is possible to position the BRE such that it intercepts the pump beam on only one pass, if desired. In the alternative where the pump beam travels through the BRE only once, a mirror M1 is oriented such that the reflected beam emerging from the BRE is separated by a small amount so that the reflected beam may be separated from the incident beam. The angle made by the counterpropagating beams in the BRE and HWP (or EOM1, as shown in FIG. 6) must be only a few degrees to ensure that the emergent and incident beams remain polarized along substantially the same axis. An alternative design, which allows the counterpropagating beams to be kept parallel, features a retroreflector in place of the mirror M1.

Figure 8:
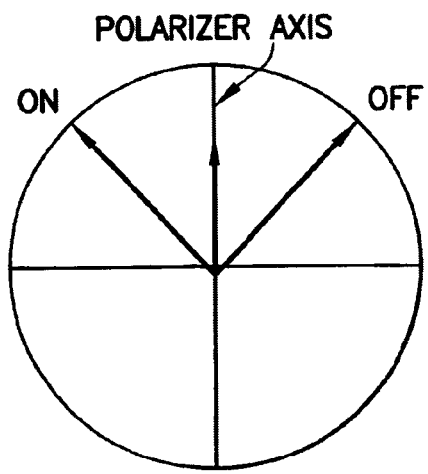
FIG. 8 depicts the electric field polarization directions for the ON and OFF states, and the polarizer axis.

A further embodiment is shown in FIG. 7. The polarization of the beam exiting EOM1 is alternated as the EOM1 is toggled between the ON/OFF states. The beam is then directed through a birefringent element BRE which gives ON/OFF transit times differing by $d(n1-n2)/c$ as described above. Polarizer P1 is oriented such that it transmits light polarized along an axis that makes an angle of forty-five degrees with respect to both orthogonal (i.e. ON/OFF) states for light exiting EOM1. This orientation is depicted in FIG. 8. FIG. 8 shows the electric field polarization directions for ON and OFF states, and the polarizer axis. In this system, the polarization, divergence, direction of propagation and spectral content of light exiting the polarizer P1 are substantially the same as those of the input beam. The exiting light intensity is one half that of the input beam.

It should be understood that the modulating signal applied to the EOM in the electrically controlled delay modulation schemes depicted in FIGS. 4 through FIG. 7 need not simply toggle between two states. That is, the modulating signal need not be limited to a rectangular pulse train; other modulation signals are also possible. In the most general case, the signal may be a pure sine wave having a frequency $f_{DIFF}$. A linearly polarized beam incident on an EOM driven by this signal will be transmitted with a linear polarization that oscillates continuously between two extrema (which depend on, among other things, the drive voltage). The drive voltage may be selected to cause the final polarization to oscillate between two orthogonal states. If this beam is now applied to a BRE as in FIG. 4, the final transmitted beam will have two components, one of which lags the other by a time as described previously, and whose relative intensities oscillate continuously. This beam may further be applied to a linear polarizer P1 as in FIG. 8, giving a final beam exiting from the system having a single linear polarization with two components having a constant relative delay, and an oscillating intensity ratio.

Additionally, it should be noted that a fixed time difference delta-t for a given birefringent crystal BRE does not exist in the preferred embodiment described in FIG. 3, since the delay stage can be easily controlled to adjust the path length difference, and hence delta-t.

Method of Operation

Operation of the apparatus produces a pump beam signal that is characterized by time delayed pulses. The measurements taken with the pump beam signal can be analyzed using known methods for the determination of the thickness of each of the layers on the sample being measured. Suitable known methods include the methods as presented by Maris et al. Enhancements to the known methods, in accordance with this invention, provide for refined calculation of film thickness.

Films that may be measured using this invention include, but are not limited to, opaque films and combinations of films. In embodiments where combinations of films are evaluated, transmissive films and other films may be measured together, where the other films provide for generation of an acoustic signal. For example, transmissive films may be measured in combination with an underlying opaque film. In this embodiment, the underlying film provides a surface or region for generation of an acoustic signal.

First Method of Operation: Using the Electro-Optic Differentiator

A first embodiment of a method of operation of a photoacoustic system as disclosed herein involves use of an apparatus that includes an electro-optic differentiator. In this embodiment, the method for determination of film thickness for a film at a measurement site on a wafer includes the steps of: loading the wafer from the cassette to the measurement stage; bringing the optical assembly of the measurement system into focus; aligning the beam spot with a measurement site; applying a half-wave voltage to the EOM at a frequency $f_{DIFF}$ and setting the time differentiation step delta-t according to a pre-determined recipe; making a measurement; recording the measurement data; analyzing the measurement data to determine the film thickness in the measurement area; and, unloading the wafer back to the cassette. In other versions of this embodiment, the manipulations of the sample, such as the loading and unloading, may be completed through means other than with a cassette system. For example, the loading and unloading may occur manually. The actual configuration of the apparatus in this regard is dependent upon, among other things, user needs.

Figure 9:
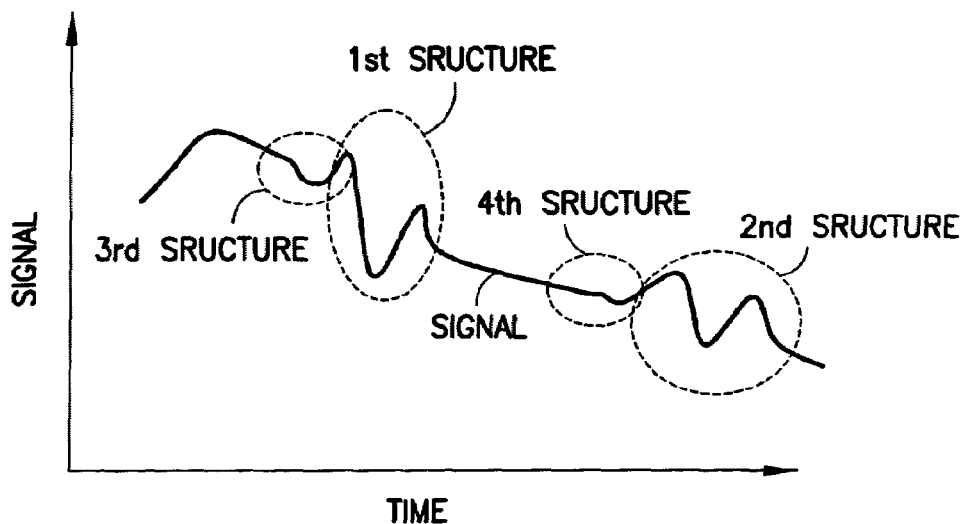
FIG. 9 is an example graph of the measured fine structure signal without using this invention; and, FIG. 10 is an example graph of the measured fine structure signal resulting from use of this invention for the sample shown in FIG. 9.

FIG. 9 represents the measured signal derived from operation in the mode as presented by Maris et al., and herein incorporated by reference. In FIG. 9, analysis of the signal reveals a first structure, a second structure, a third structure and a fourth structure. The first and second structures result from the stress field propagating through a relatively thick layer, while the third structure and fourth higher frequency structures stem from the presence of a thin layer underneath the thick layer.

Figure 10:
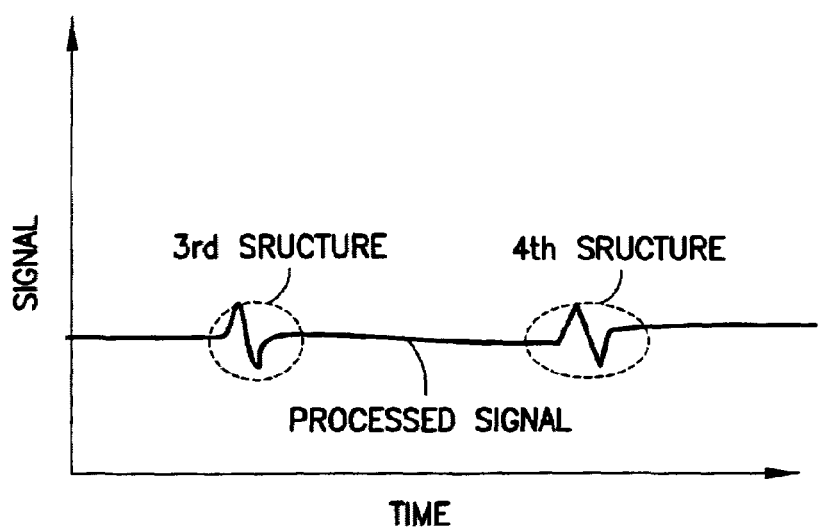

FIG. 10 shows a processed signal in which the high frequency structures associated with the buried thin layer have been enhanced. The resulting signal is derived from applying the apparatus and method of the present invention. A time delay difference delta-t is chosen such that delta-t is approximately $d_{FILM}/5\, v_S$, where $d_{FILM}$ and $v_S$ are the thickness and the velocity of sound in the thin buried layer, respectively.

Methods for analysis of measurement data to determine the film thickness are known. U.S. Pat. No. 5,748,318 "Optical Stress Generator and Detector" by Maris et al., issued on May 5, 1998, and incorporated by reference, provides a method for characterization of thin films.

The present invention further includes the steps of: setting the differentiation time step delta-t to be optimally sensitive to the higher-frequency features (for example, features found in structures three and four as presented in FIG. 9 and FIG. 10); analyzing the differentiated data using the derivative of the technique of Maris et al. to obtain the thin layer thickness with a high degree of precision; and fixing (or holding constant) that layer thickness and analyzing the non-differentiated signal using another technique, such as the technique presented by Maris et al., to obtain the thick layer thicknesses. Regarding the phrase "derivative of the technique of Maris", this phrase refers to the numerical derivative with respect to time delay of the simulation technique presented by Maris.

Second Method of Operation: Using the Birefringent Element

A second embodiment of a method of operation of the photoacoustic system disclosed herein involves use an apparatus that includes an electro-optic signal generator. In this embodiment, the method for determination of film thickness for a film at a measurement site on a wafer includes the steps of: loading a wafer from the cassette to the measurement stage; bringing the optical assembly of the measurement system into focus; aligning the beam spot with a measurement site; applying a half-wave voltage to an electro-optic modulator according to a pre-determined recipe to induce a fixed time delay delta-t between the vertically polarized pulse (which exits the birefringent crystal first) and the horizontally oriented pulse (which exits the birefringent crystal second); making a measurement; recording the measurement data; analyzing the measurement data using a known method to determine the film thickness in the measurement area; and, unloading the wafer back to the cassette. Here also, other versions of this embodiment may be realized. For example, the manipulations of the wafer, such as the loading and unloading, may be completed through means other than with a cassette system. For example, the loading and unloading may occur manually. The actual configuration of the apparatus in this regard is dependent upon, among other things, user needs.

The second embodiment also includes the further steps of: analyzing the differentiated data using the derivative of the technique of Maris et al. to obtain the thin layer thickness with a high degree of precision; and fixing (or holding constant) that layer thickness and analyzing the non-differentiated signal using another technique, such as the technique presented by Maris et al., to obtain the thick layer thicknesses. Regarding the phrase "derivative of the technique of Maris", this phrase refers to the numerical derivative with respect to time delay of the simulation technique presented by Maris.

This invention preferably uses synchronous detection techniques where, for example, the detected probe signal is synchronously detected with a frequency used for driving the time differentiation system. The time differentiation system effectively varies or dithers the time delay between the pump pulse and the following probe pulse by some desired amount, such as from about 0.1 picoseconds to some number of picoseconds (e.g. 1–10 picoseconds). This rapid dithering of the time delay, which may be considered to be equivalent to rastering the pump pulses, can occur at the frequency used in the prior art for amplitude modulating the pump pulse train (e.g. about 5 MHz) or at higher frequencies.

Advantages that arise from the use of these teachings include, but are not limited to, the following: there is no phase difference over the beam path; the signal to noise ratio is increased over existing systems; and the sensitivity of the optical metrology system is enhanced for thin layer detection, especially when adjacent to thicker layers.

Other advantages of the teachings herein include, but are not limited to, the ability to make measurements using multiple wavelengths in the photoacoustic system, and the ability to ascertain the thickness of transmissive layers in a film.

It can thus be appreciated that while the invention has been particularly shown and described with respect to preferred embodiments thereof, it will be understood by those skilled in the art that changes in form and details may be made therein without departing from the scope and spirit of the invention.

What is claimed is:

1. A photoacoustic measurement system for measuring the thickness of at least one film layer in a sample comprising:
   a time differentiation system comprising an electro-optic modulator and two optical paths of different optical lengths to induce a time delay between a first pump beam pulse traversing a first optical path and a probe beam, and a second time delay between a second pump beam pulse traversing a second optical path and a probe beam; wherein, the pump beam pulses are directed to a measurement site of the sample to obtain a signal representing the thickness of at least one film layer at the measurement site.

2. A photoacoustic measurement system according to claim 1, wherein the time differentiation system further comprises a half wave plate.

3. A photoacoustic measurement system according to claim 1, wherein the time differentiation system further comprises a mirror.

4. A photoacoustic measurement system according to claim 1, wherein the time differentiation system further comprises a polarizer.

5. A photoacoustic measurement system according to claim 1, wherein the time differentiation system further comprises a retroreflector.

6. A photoacoustic measurement system according to claim 1, wherein the frequency of the pump beam time differentiation ranges from about one kHz up to about one GHz.

7. A photoacoustic measurement system for measuring the thickness of at least one film layer in a sample comprising:
   a time differentiation system comprising a birefringent element in optical series with an electro-optic modulator, and a time-variable voltage source coupled to the electro-optic modulator, to induce a time delay delta-t between differently polarized pump beam pulses; wherein, the pump beam pulses form a time-differentiate beam that is directed to a measurement site of the sample to obtain a signal representing the thickness of the at least one film layer at the measurement site.

8. A photoacoustic measurement system according to claim 7, wherein the electro-optic modulator functions as a half wave plate.

9. A photoacoustic measurement system according to claim 7, wherein the time differentiation system further comprises a mirror.

10. A photoacoustic measurement system according to claim 7, wherein the time differentiation system further comprises a polarizer.

11. A photoacoustic measurement system according to claim 7, wherein the time differentiation system further comprises a retroreflector.

12. A photoacoustic measurement system according to claim 7, wherein the frequency of the pump beam time differentiation ranges from about one kHz up to about one GHz.

13. A method for determining the thickness of at least one film layer contained within a stacked film layer using a photoacoustic measurement system, the method comprising:
   aligning a beam spot with a measurement site on the stacked film layer;
   applying a time-varying voltage to an electro-optic modulator to generate a time differentiated measurement beam, said time differentiated measurement beam comprising a first pump beam traversing a first optical path and a second pump beam traversing a second optical path of optical length different from the first;
   making a measurement at the measurement site using the first and second beams;
   recording measurement data; and,
   analyzing the measurement data to determine the thickness of the at least one film layer at the measurement site.

14. The method according to claim 13, wherein analyzing comprises:
   setting a time differentiation step to be sensitive to frequency selective signal features arising from the presence of a thin film layer contained within the stacked film layer to obtain differentiated data;
   analyzing the differentiated data to obtain the thickness of the thin film layer; and,
   holding the thickness of the thin layer constant while analyzing non-differentiated data to determine the thickness of a thick film layer contained within the stacked film layer.

15. The method according to claim 13, wherein the stacked film layer comprises a semiconductor.

16. A method for determining the thickness of at least one film layer contained within a stacked film layer using a photoacoustic measurement system, the method comprising:
   aligning a beam spot with a measurement site on the stacked film layer;
   applying a time-varying voltage to an electro-optic modulator to induce a time delay delta-t between a vertically polarized pump beam pulse and a horizontally polarized pump beam pulse thus forming a time differentiated beam;
   making a measurement at the measurement site with the time differentiated beam;
   recording measurement data; and,
   analyzing the measurement data to determine the thickness of the at least one film layer at the measurement site.

17. The method according to claim 16, wherein the analyzing comprises:
   setting the time delay to be optimally sensitive to the frequency selective signal features arising from the presence of a thin film layer contained within the stacked film layer to obtain differentiated data;
   analyzing the differentiated data to obtain the thickness of a thin film layer contained within the stacked film layer; and,
   holding the thin layer thickness constant while analyzing non-differentiated data to determine the thickness of a thick film contained within the stacked film layer.

18. The method according to claim 16, wherein the stacked film layer comprises a semiconductor.

* * * * *